(12) United States Patent
Chigurupati et al.

(10) Patent No.: US 9,149,491 B2
(45) Date of Patent: Oct. 6, 2015

(54) REDUCED TOXICITY IN ALCOHOLIC BEVERAGES

(71) Applicant: CHIGURUPATI TECHNOLOGIES PRIVATE LIMITED, Hyderabad, Andhra Pradesh (IN)

(72) Inventors: Harsha Chigurupati, Andhra Pradesh (IN); Manish Radheshyam Biyani, Andhra Pradesh (IN); Biswajit Auddy, Andhra Pradesh (IN)

(73) Assignee: Harsha Chigurupati, Hyderabad (IN)

( * ) Notice: Subject to any disclaimer, the term of this patent is extended or adjusted under 35 U.S.C. 154(b) by 0 days.

(21) Appl. No.: 14/376,039

(22) PCT Filed: Apr. 28, 2014

(86) PCT No.: PCT/IB2014/061051
§ 371 (c)(1),
(2) Date: Jul. 31, 2014

(87) PCT Pub. No.: WO2014/177989
PCT Pub. Date: Nov. 6, 2014

(65) Prior Publication Data
US 2015/0141358 A1 May 21, 2015

(30) Foreign Application Priority Data
Apr. 29, 2013 (IN) .......................... 1894/CHE/2013

(51) Int. Cl.
| A61K 31/704 | (2006.01) |
| A61K 31/047 | (2006.01) |
| A61K 31/7004 | (2006.01) |
| A61K 31/7016 | (2006.01) |
| C12G 3/04 | (2006.01) |
| C12G 3/06 | (2006.01) |

(52) U.S. Cl.
CPC ............ *A61K 31/704* (2013.01); *A61K 31/047* (2013.01); *A61K 31/7004* (2013.01); *A61K 31/7016* (2013.01); *C12G 3/04* (2013.01); *C12G 3/06* (2013.01); *A23V 2002/00* (2013.01)

(58) Field of Classification Search
CPC ............ A61K 31/704; A61K 31/047; A61K 31/7004; A61K 31/7016; A61K 2300/00; C12G 3/04; C12G 3/06; A23V 2200/334; A23V 2250/252; A23V 2250/628
USPC ........................................................ 514/33
See application file for complete search history.

(56) References Cited

U.S. PATENT DOCUMENTS

| 4,393,200 A | 7/1983 | Miyashita et al. |
| 4,868,207 A | 9/1989 | Shi-jie |
| 2005/0095233 A1* | 5/2005 | McCleary et al. ........... 424/94.1 |
| 2006/0160754 A1 | 7/2006 | Yoshikawa et al. |
| 2009/0162483 A1* | 6/2009 | Constantine et al. ........... 426/62 |
| 2010/0037353 A1 | 2/2010 | Suzuki et al. |

FOREIGN PATENT DOCUMENTS

| CN | 1448497 A | 10/2003 |
| CN | 101744865 B | 7/2012 |
| EP | 0270690 B1 | 5/1991 |
| EP | 0502554 A2 | 9/1992 |
| JP | 05-017349 A | 1/1993 |
| JP | 06014746 | 1/1994 |
| JP | 09-143085 A | 6/1997 |
| KR | 1020050032807 A | 4/2005 |
| WO | WO 89/04165 A1 | 5/1989 |
| WO | WO 2010/122482 A1 | 10/2010 |

OTHER PUBLICATIONS

Scientific Committee on Food, Opinion of the Scientific Committee on Food on Glycyrrhizinic Acid and Its Ammonium Salt. European Commission Health & Consumer Protection Directora Te•General, SCF/CS/ADD/EDUL/225 Final Apr. 10, 2003.*
Shibayama, Y. Prevention of Hepatotoxic Responses to Chemicals by Glycyrrhizin in Rats. Exp. Mol. Pathol. 1989, vol. 51, No. 1, pp. 48-55.
Wang, G.S. et al. The Protective Action of Glycyrrhiza Flavonoids Against Carbon Tetracholirde Hepatotoxicity in Mice. Yao Xue Xue Bao. 1993, vol. 28, No. 8, pp. 572-576.
Kim, S.C. et al. Cytoprotective effects of Glycyrrhizae radix extract and its active component liquiritigenin against cadmium-induced toxicity (effect on bad translocation and cytochrome c-mediated PARP cleavage). Toxicology. 2004, vol. 197, No. 3, pp. 239-251.
Database WPI, Week 200960, Thomson Scientific, London, GB; AN 2008-022478, XP002732942, & KR 2008 0002772 U (Bang K D), Jul. 22, 2008 abstract.
Database WPI, Week 201240, Thomson Scientific, London, GB; AN 2012-G22740, XP002732943, & CN 102 450 712 A (Zhao Q); May 16, 2012; abstract.
CN 100 455 215 C (Xie Chunsheng [CN]; Chunsheng Xie [CN]) Jan. 28, 2009 the whole document.
CN 100 539 877 C (Huange Hengsen [CN] Henghsen Huang [CN]) Sep. 16, 2009, abstract.
WO 2007/081115 A1 (Seoul Nat Univ Ind Foundation [KR]; Kim Sang Geon [KR]; Kim Sang Chan) Jul. 19, 2007 paragraphs [0001], [0022], [0042], [0058], [0084]-[0088], [0287].

(Continued)

*Primary Examiner* — Mark Shibuya
*Assistant Examiner* — Yih-Horng Shiao
(74) *Attorney, Agent, or Firm* — Daniel Christopherson

(57) ABSTRACT

The present invention relates to reduced toxicity of functional alcoholic beverage composition comprising distilled alcohol, deionized water, 18β-Glycyrrhizin or 18α-Glycyrrhizin and a sugar alcohol or sugars, having pH in the range of 4.0-9.0. More particularly, alcoholic beverage composition comprises distilled alcohol, deionized water, 18β-Glycyrrhizin or 18α-Glycyrrhizin and a sugar alcohol/sugars as hepato-protectants. The present invention provides an alcoholic beverage for reducing hepatotoxicity caused by its consumption and a process to manufacture the said alcoholic beverage.

23 Claims, No Drawings

(56) References Cited

OTHER PUBLICATIONS

Francis J. Martin and Robert C. MacDonald, Lipid Vesicle-Cell Interactions: I. Hemagglutination and Hemolysis, The Jounal of Cell Biology, 1976, pp. 494-505, vol. 70, The Rockefeller University Press, New York City, NY.

Sanjai Saxena, Glycyrrhiza glabra: Medicine over the millennium, Natural Product Radiance, Mar. 24, 2005, pp. 1-10, vol. 4(5), National Institute of Science Communication and Information Resources, New Delhi, India.

Asha Roshan et al., Phytochemical Constituent, Pharmacological Activities and Medicinal Used Through the Millennia of Glyrrhiza Glabra Linn: A Review, International Research Journal of Pharmacy, Nov. 7, 2012, pp. 45-55, vol. 3(8), Moksha Publishing House, India.

Vijay Singh Jatav et al., Recent Pharmacological Trends of Glycyrrhiza glabra Linn, International Journal of Pharmaceutical Frontier Research, Apr.-Jun. 2011, pp. 170-185, vol. 1(1), International Journal of Pharmaceutical Frontier Research, India.

Hiroshi Hojo and Jun Sato, Antifungal Activity of Licorice (*Glycyrrhiza glabra*) and Potential Applications in Beverage, Foods & Food Ingredients Journal of Japan, 2002, p. 1, vol. 203, The Japan Foods Chemical Research Foundation, Japan.

Hitoshi Sato et al., Therapeutic basis of glycyrrhizin on chronic hepatitis B, Antiviral Research, Jan. 17, 1996, pp. 1-7, vol. 30, Elsevier, Amsterdam, Netherlands.

* cited by examiner

REDUCED TOXICITY IN ALCOHOLIC BEVERAGES

The following specification particularly describes the invention and the manner in which it is to be performed.

FIELD OF INVENTION

The present disclosure provides an alcoholic beverage having reduced hepato-toxicity. The invention also relates to a process for the preparation of the said beverage.

BACKGROUND OF THE INVENTION

Ethanol consumption could lead to 60 medical conditions. Acute as well as chronic toxic effect of ethanol may ensue in irreversible organ damage (Das S. K. et. al., Indian journal of Biochemistry & Biophysics, 2010, Vol. 47, 32). The widely accepted forms of alcoholic liver diseases (ALD) are simple fatty liver (steatosis), which is reversible with abstinence, fatty liver accompanied by inflammation (steato-hepatitis) leads to scar tissue formation (fibrosis), the destruction of the normal liver structure (liver cirrhosis), which may or may not improve with abstinence and subsequently lead to liver cancer (hepatocellular carcinoma). In 2010, WHO suggests 10% of the adult population in the United States suffering from alcohol use disorders and liver cirrhosis is the $12^{th}$ leading cause of death in United States (Alcohol and Health, Focus on: Alcohol and the Liver, 2010, Vol. 33, No. 1 and 2, 87). It is known that 5% of the ethyl alcohol i.e. ethanol (hereinafter alcohol), ingested by a human being is excreted unchanged while the remaining 95% is degraded to acetaldehyde. Alcohol is rapidly absorbed from the GI tract. In fasting state the peak blood alcohol concentration reaches within 30 minutes. Distribution is rapid with tissue levels approximating blood concentrations. Liver accounts for nearly 90% of alcohol metabolism the remainder is excreted through the lungs & urine. The typical adult can metabolize 7-10 g of alcohol/hour (U.S. Pat. No. 7,666,909B2).

The primary pathway of alcohol metabolism, when consumed in low to moderate amount, is mainly catalyzed in the cytoplasm of hepatocytes by alcohol dehydrogenase (ADH) to form acetaldehyde. The accumulation of NADH (excess reducing equivalents) in the liver plays a role in liver damage seen more prominently with chronic alcohol use. Acetaldehyde produced through microsomal ethanol oxidation system (MEOS) initially represents a minor pathway of ethanol oxidation probably accounting for less than 10%, of the liver capacity to oxidize ethanol.

At higher alcohol level (>100 mg/dl), MEOS is dependent on CYP450 (2E1, 1A2 & 3A4) plays significant role in alcohol metabolism using NADPH as a cofactor & $O_2$. Catalase is especially capable of oxidizing ethanol in fasting state in the presence of hydrogen peroxide generating system. Acetaldehyde is oxidized in the liver via mitochondrial nicotinamide adenine dinucleotide ($NAD^+$) dependent aldehyde dehydrogenase (ALDH) to acetate. Activity of ALDH is nearly 3 times lower that ADH, hence accumulation of Acetaldehyde takes place. Acetate is further metabolized to acetyl CoA and can enter min TCA cycle or synthesis fatty acids. Each of these pathway results in the formation of free radicals (like reactive oxygen species {ROS}) with concomitant changes in the cells redox state (i.e. in the ratio of NADH to $NAD^+$ results in production of more NADH (Nicotinamide Adenine Dinucleotide ($NAD^+$) reduced by two electrons). The cell has a limited capacity to oxidize NADH back to $NAD^+$ in mitochondrial respiratory chain at the maximum capacity of this system, which determines the kinetics of the reaction. The redox state in relation to alcohol metabolism causes inhibition of $NAD^+$-mediated enzyme reactions typical to the normal metabolism of the hepatocyte. The citric acid cycle is affected the most as it gets inhibited. This leads to positive NADH/NAD ratio, which is considered the most important reason for the development of alcohol-induced fatty liver. The maximum capacity of the mitochondrial respiratory chain depends on the overall level of metabolism of the body. The consequence of altered redox state includes Hypoxia (oxygen deficit cell). The other plausible pathway of alcohol induced hepatotoxicity includes excess production of pro-inflammatory cytokines by gut-endotoxin stimulated Kupffer cells. ROS is mainly generated in association with the mitochondrial electron transport system; it is also produced by CYP2E1 and by activated Kupffer cells in the liver. Both acute and chronic alcohol consumption can increase ROS production, which leads to oxidative stress through a variety of pathways mentioned above [(Zakhari, S. Alcohol Research & Health, 2006, 29, 4, 245), (Wheeler M. D. et al, Free Radical Biology & Medicine, 2001, Vol. 31, No. 12, 1544), (Koop, D. R., Alcohol Research & Health, 2006, 29, 4, 274), (U.S. Pat. No. 7,666,909B2)].

The mechanisms involved by which alcohol causes cell injury are complex and combination of several inter-related pathways. ROS react primarily with the cell membrane (tight junction becomes more permeable) and in turn leaks lipopolysaccharides (LPS), as a consequence impaired gut structural integrity. The increases in transaminase enzymes [aspartate amino-transferase (AST) and alanine aminotransferase (ALT)] indicate cellular leakage and loss of functional integrity of cell membrane (Yue et. J, 2006). Loss of cellular integrity affects hepato-biliary function leading to elevated alkaline phosphatase (ALKP) activities with concurrent increase in serum bilirubin level and decrease in the total plasma protein content. Both increases and decreases in the levels of ROS can lead to apoptosis of hepatocytes (Wheeler M. D. Alcohol Res. Health, 2003; 27, 300). For the cell to function normally, GSH is critical to protect itself against ROS generated during activity of the mitochondrial respiratory chain. Alcohol consumption rapidly depletes GSH levels; alcohol interferes with Cytochrome c to leak from the mitochondria into the cytosol, which can activate enzymes known as caspases that can trigger apoptosis.

ROS induces LPO [ROS reacting with Malondialdehyde (MDA), 4-hydroxy nonenal (HNE)] and recognized as important starting place of hepatocytes damage. Endotoxin-activated Kupffer cells affects mitochondria leading to release of ROS (hydrogen peroxide radical, hydroxyl radical, particularly superoxide radical) and several cytokines (viz., Tumour necrotic factor {TNF-α}) leading to hepatocytes necrosis and apoptosis. It has been established by clinical studies that patients with alcoholic liver disease have increased levels of the inflammatory cytokines IL-1, IL-6, and TNF-α as well as the chemokine IL-8 and other cytokines.

Alcohol might enhance the sensitivity of hepatocytes, consequently which could lead to an increased production of ROS in the mitochondria. ROS could activate a regulatory protein called nuclear factor kappa B (NFκB), which plays critical role in regulation of immune response and controls the activities of numerous genes, including those that expresses TNF-α & its receptor as well as genes encoding proteins that promote apoptosis. Thus, a vicious cycle would be established in the hepatocytes: TNF-α promotes ROS production, which in turn activates NFκB, leading to enhanced production of additional TNF-α and its receptor as well as to production of factors that promote apoptosis. This cycle eventually alters the structure of the hepatocytes, impairs their function, and can lead to hepatocyte apoptosis. TNF-α also facilitates hepatocyte regeneration by promoting the proliferation [(Wheeler M. D. Alcohol Res Health, 2003; 27, 300), (Molina P., Happel, K. I., Zhang P., Kolls J. K., Nelson S., Focus on: alcohol and the immune system. Alcohol Res. Health, 2010, 33 (1 & 2), 97)1)].

TGF-β (transforming growth factor beta) might be involved in the development of alcohol-induced liver damage, which could cause the hepatocytes to produce molecules like trans-glutaminase, cytokeratins that are normally responsible for giving the cells their shapes. In excess, these molecules are cross-linked to form microscopic structures called Mallory bodies, which are markers of alcoholic hepatitis. TGF-β can also contribute to liver damage by activating stellate cells. In a normal state, these cells primarily serve to store fat and vitamin A in the liver. When activated, stellate cells produce collagen, the major component of scar tissue it leads to the development of liver fibrosis. Alcohol might trigger the activation of TGF-β and thereby contribute to the initiation of apoptosis if this molecule enters the blood in higher concentrations (Wheeler M. D., Alcohol Res. Health, 2003; 27, 300).

Acetaldehyde or ROS with DNA or protein or protein building blocks and ROS with MDA or MAA (mixed MDA-acetaldehyde-protein adduct) or HNE etc. in the cell could form stable or unstable adduct, which could be carcinogenic, immunogenic, induce inflammatory process, damage to the mitochondria etc. [(Zakhari, S. Alcohol Research & Health, 2006, 29 (4)245); (D. Wu, Alcohol Research & Health, 2106, 27, 4, 277); (Wheeler M. D., Alcohol Res. Health, 2003; 27, 300); (Molina P., Happel K. I., Zhang P., Kolls J. K., Nelson S., Focus on: alcohol and the immune system; (Alcohol Res. Health, 2010, 33, Vol. 1 & 2, 97); (Neuman M. G., Cytokine-central factor in alcoholic liver disease, Alcohol Res. Health, 2003, 27, 307)].

Varieties of endogenous enzymatic and non-enzymatic mechanisms have evolved to protect cells against ROS. This includes the superoxide dismutases (SOD), which remove $O_2^-$; Catalase (CAT) and the glutathione peroxidase ($GP_X$) system, which remove $H_2O_2$ and non-enzymatic low-molecular-weight antioxidants such as reduced glutathione (GSH), Vitamin E, Vitamin C, Vitamin A, Ubiquinone, Uric acid, and bilirubin. But these are capable to protect the cells to limited extent. Additional protection could be achieved by orally administrating the glutathione precursor like S-adenosyl-L-methionine (SAMe), N-acetyl cysteine (NAC) or anti-oxidant like Vitamin E, Vitamin C, plant bioactives (gallic acid, quercetinete) etc. (D. Wu, Alcohol Research & Health, 2006, 27, 4, 277).

PRIOR ART OF THE INVENTION

Literature discloses alcoholic beverages with various types of additives. The following literature exists in the field of this invention and has been considered in entirety.

US Patent Publication No. 20100086666 discloses alcoholic beverages in which a protein like casein hydrolysate to enhance smoother taste and gives some nutritional benefit to the consumer.

Das S. K. et. al. (Indian Journal of Biochemistry & Biophysics, 2010, vol 47, 32) describes concomitant treatment of resveratrol or vitamin E with alcohol in mice ameliorates; alcohol induced oxidative stress, angiogenesis process and aid in controlling immune-modulatory activity.

US Patent Publication No. 20100086666 discloses alcoholic beverages, which comprises phenol like epigallocatechingallate (EGCG), epigallocatechine (EGC), epicatechin (EC), epicatechingallate (ECG), proanthocyanin, tannin and quercetin etc. known to reduce oxidative stress by scavenging free radicals generated by alcohol.

U.S. Pat. No. 7,666,909B2 reveals alcoholic beverages comprising D-Glyceric acid and its salts enhancing the metabolism of alcohol reducing the adverse event caused due to alcohol consumption.

GA or Matrine (Mat) alkaloid isolated from S. flavescens alone, or GA+Mat, when administered to rat models of hepatic fibrosis induced by abdomen injection of dimethyl nitrosamine (DMN) in acetaminophen overdosed mice, reduces the mortality by attenuating acetaminophen-induced hepatotoxicity. This is probably due to reduced number and area of γ-GT positive foci. In addition, GA+Mat had a protective effect on immunosuppression, a strong non-specific anti-inflammatory effect, and an effect of reducing the incidence of sodium and water retention (W. Xu-yingae, Chemico-Biological Interactions, 181 (2009) 15-19).

WO No. 2008/055348A1 discloses that alcoholic beverages comprising turmeric reduces hangover.

Das S. K. et al. (Indian Journal of Experimental Biology, 2006, Vol 44, 791) reveals concomitant treatment of lecithin with Vitamin B complex or Vitamin E with alcohol in Wistar rats was performed. It was established that lecithin with Vitamin B complex with alcohol was promising therapeutic approach than Vitamin E with alcohol in allaying oxidative stress.

El-Fazaa S. et al. (Alcoholism & Alcoholism, 2006, Vol. 41, No 3, 236) exemplifies alcoholic beverages comprising resveratrol inhibits the alcohol induced lipid peroxidation and have protective effect against injury.

WO1989004165A1 or EP0336960A4 divulges alcoholic beverages with combination of any one or more sugars from the group consisting of D-Galactose, D-Lactose, D-Xylose. L-Fructose, D-Mannitol, D-Sorbitol, D-Glucose etc.

JP06014746 discloses alcoholic beverages comprising a glycoside of quercetin, divalent metallic ion and licorice extract (Glycyrrhizin). This beverage enhances alcohol metabolism and has hepatopathy-suppressive activity, due to ethanol and acetaldehyde. Thus, it reduces hangover.

CP Patent Publication No. 1736270 discloses liver-protecting drink constituting Chitosan oligosaccharide, glycyrrhizin, aqueous extract of kudzuvine flower and aqueous extract of hovenine.

US Patent Publication No. 20090196951 reveals alcoholic beverages comprising resveratrol a strong anti-oxidant, also activates the Sirtuin 1 (SIRT1) and Peroxisome proliferator-activated (PPAR)-gamma coactivator-1[PGC-1'] gene, which are key regulator of energy and metabolic homeostasis.

JP2008266203 and EP0502554 discloses an increase in amount of an enzyme activity of the Reactive oxygen species (ROS) scavenging enzyme group such as superoxide dismutase, catalase or peroxidase with one or more kinds of substances selected from the group consisting of Erythritol, Mannitol, Sorbitol and Xylitol.

CN1448497 discloses an alcoholic drink comprising of ethanol and Glycyrrhizin, but a synergistic mixture of alcohol with hepato-protectants that include certain sugar alcohols or sugars as integral part of the present composition, apart from Glycyrrhizin has not been described.

CN101744865 discloses a method of producing a liver protecting tablet comprising Xylitol and Glycyrrhizin. CN101744865 focuses on a method for preparing Xylitol liver tablets and nowhere demonstrates biological activity of such tablets. Moreover, the present patent is focused to an alcoholic beverage having reduced toxicity and a method of preparing the same. The present application demonstrates a synergistic mixture of alcohol with hepato-protectants that include certain sugar alcohols or sugars as integral part of the composition and such synergistic mixture offers a good degree of hepato-protection.

Various other prior art documents are known (US 20080226787, U.S. Pat. No. 3,282,706, U.S. Pat. No. 1,720,329, U.S. Pat. No. 4,537,763, U.S. Pat. No. 8,524,785) where glycyrrhizin and sugar alcohols like Mannitol, Erythritol, Xylitol etc. have been used for imparting various functions in the beverages as non-nutritive sweetening agent having low calorific value or as flavoring agent, but the aspect of hepato-protection has not been disclosed.

Documents are available in prior art, which show that Glycyrrhizin, sugar alcohols and sugars are independently known to exhibit hepato-protective activity, but their combination to exhibit synergistic hepato-protection has not been reported so far. Applicant in this application reports for the first time synergistic activity imparted by a combination of 18β or α-Glycyrrhizin and sugar alcohols, more particularly 18β/α-Glycyrrhizin and D-Mannitol exhibiting exemplified synergistic hepato-protection to provide a beverage with reduced toxicity.

SUMMARY OF THE INVENTION

The present disclosure relates to an alcoholic beverage, particularly to alcoholic distilled spirits like vodka, flavored vodka, whisky, etc. having reduced hepato-toxicity comprising distilled alcohol, deionized water, glycyrrhizin and a sugar alcohol or sugar having a pH in the range of 4.0-9.0.

More particularly the invention provides an alcoholic beverage having reduced hepatotoxicity comprising distilled alcohol, deionized water, 18β-Glycyrrhizin or 18α-Glycyrrhizin and a sugar alcohol or sugar. The invention also relates to a process for the preparation of the said beverage. The exemplified reduced hepato-toxicity provided by the beverage has been achieved by synergistic hepato-protection exhibited by the combination of 18β or 18α-glycyrrhizin and a sugar alcohol/sugar present in the said alcoholic beverage.

OBJECTS OF THE INVENTION

An object of the present invention is to provide an alcoholic beverage having reduced toxicity.

Another object of the present invention is to provide an alcoholic beverage having synergistic activity and providing enhanced hepato-protection.

Yet another object of the present invention is to provide a beverage comprising hepato-protective agent(s) to achieve the reduced hepato-toxicity.

Yet another object of the present invention is to provide an alcoholic beverage comprising 18β-Glycyrrhizin or 18α-Glycyrrhizin to achieve the reduced hepato-toxicity.

Yet another object of the present invention is to provide an alcoholic beverage comprising hepato-protective agent(s) like sugar alcohols and sugar.

Yet another object of the present invention is to provide an alcoholic beverage comprising the sugar alcohols selected from D-Mannitol, D-Erythritol, D-Xylitol and like.

Yet another object of the present invention is to provide an alcoholic beverage comprising sugars selected from D-Xylose, D-Mannose, D-Sucrose and D-Lactose.

Still another object of the present invention is to provide an alcoholic beverage comprising pH adjusting agent(s), flavoring agent(s).

Further object of the present invention is provide an alcoholic beverage comprising optionally of the flavoring agents selected from vanilla, strawberry and like.

Still another object of the present invention is to provide an alcoholic beverage having acceptable taste, flavor, odor, clarity and buzz factor.

Another important object of the present invention is to provide a process for the preparation of alcoholic beverage composition comprising (a) alcohol or alcohol:water mixture (b) 18β-Glycyrrhizin/18α-Glycyrrhizin (c) sugar alcohol or sugar (d) pH adjusting agents and optionally a flavoring agent.

Still another object of the present invention provides an alcoholic beverage composition having enhanced hepato-protection.

The alcoholic beverage is for use in a method of amelioration of diseases involving acute and chronic alcoholic toxicity like alcoholic liver diseases (ALD) like steatosis.

BRIEF DESCRIPTION OF THE TABLES

Table 1: % Protection of D-Mannitol
Table 2: % Protection of D-Xylitol & D-Erythritol
Table 3: % Comparative Protection of 18β and 18α-Glycyrrhizin
Table 4: % Protection and % Synergism of 18β-Glycyrrhizin-Mannitol combinations
Table 5: Comparative % Protection and % Synergism of 18β or 18α-Glycyrrhizin-Mannitol combinations
Table 6: Comparative % Protection and % Synergism of 18β-Glycyrrhizin-Mannitol, Xylitol & Erythritol)
Table 7: Comparative data of % Protection and % Synergism of (18β Glycyrrhizin/Mannitol, Xylitol & Erythritol)
Table 8: % Protection of Sucrose, Mannose, Xylose & Lactose
Table 9: % Protection and % Synergism of (18β-GA: Sucrose, Mannose, Xylose & Lactose)

DETAILED DESCRIPTION OF THE INVENTION

Accordingly, the present invention provides a beverage, more specifically an alcoholic beverage having reduced hepato-toxicity comprising distilled alcohol, deionized water, 18β or 18α-Glycyrrhizin and a sugar alcohol or sugar and having pH in the range of 4.0-9.0. More particularly the hepato-toxicity is caused by the intake of alcohol. The reduced hepatotoxicity of the beverage of the present invention is achieved by the enhanced hepato-protective activity provided by the synergistic combination of 18β or 18α-Glycyrrhizin and a sugar alcohol or Glycyrrhizin and a sugar incorporated in the said alcoholic beverage. The synergistic effect of the components has been established by dose dependent study for hepato-protection of 18β or 18α-Glycyrrhizin, sugar alcohol and a combination of Glycyrrhizin and sugar alcohol/sugar by performing experiment on animal models.
Ingredient Description:
Glycyrrhizin (or Glycyrrhizic acid or Glycyrrhizinic acid: abbreviated as GA) is the chief sweet-tasting constituent of *Glycyrrhiza glabra* (liquorice) root. It has also been given intravenously in Japan as a treatment for hepatitis C and as an emulsifier and gel-forming agent in foodstuff and cosmetics. Glycyrrhizin (GA) is a triterpenoid saponin glycoside. It is available as in racemic or pure form of 2 isomers: 18β-Glycyrrhizin and 18α-Glycyrrhizin. Hepato-protective mechanism of GA is due to its aglycone, glycyrrhetic acid, which inhibits both free radical generation as well as lipid peroxidation. 18α-GA has anti-hepato fibrosis effect—it is frequently used as a hepato-protective agent. The sweetness of GA has a slower onset than sugar, and lingers in the mouth for some time. GA is partly absorbed as an intact drug. (W. Xuyinga et. al.) Chemico-Biological Interactions 181 (2009) 15-19), (T, Zing et. al. Chinese Journal of Modern Applied Pharmacy 2006, 02, 15-19). GA and its metabolites exhibit steroid-like anti-inflammatory activity, due, in part, to inhibition of Phospholipase A2 activity, an enzyme critical to numerous inflammatory processes. They inhibit hepatic metabolism of aldosterone and suppress hepatic 5-α-reductase. Because Cortisol and aldosterone bind with the same affinity to the mineralocorticoid receptor, an increase in renal Cortisol will result in a hyper-mineralocorticoid effect (Akamatsu, H. Planta Med., 1991, 57: 119-121), (Armanini, D., Clin. Endocrinol. 1983, 19: 609).

GA completely suppressed viral antigen expression possibly by causing a decrease in the negative charge on the cell surface and/or by decreasing the membrane fluidity thereby preventing Hepatitis A virus entry in cells by receptor mediated endocytosis (W. Xu-Yinga et. al., Chemico-Biological Interactions 181 (2009) 15-19).

GA induces phase II enzymes involved in the detoxification and excretion of carcinogenic or toxic substances and other antioxidant enzymes responsible for maintaining a balanced state between free radicals/oxidants and the antioxidants within the cellular environment. Oxidative injury in AR mice (Aldose reducrase deficient mice) is reduced by GA, by increasing GSH content and decreased MDA formation in a dose dependent manner. Concomitant decreases were observed in glutathione peroxidase (GPx), catalase (CAT), total antioxidant capacity (TAOC) and SOD activities in AR mice. IFN-α, or type II interferon, is a cytokine that is critical for innate and adaptive immunity against viral and intracellular bacterial infections and for tumour control. GA led to a significant, increase of IFN-α level in medicine treated mice. IL-4 is a cytokine that induces differentiation of naive helper T cells (Th0 cells) to Th2 cells. Upon activation by IL-4, Th2 cells subsequently produce additional IL-4 (Xiao-Lan Li *Int. J. Mol. Sci.* 2011, 12, 905). GA could increase infection resistance as [monocyte chemo-attractant (chemotactic) protein-1] is a CC chemokine MCP-1 inhibitor (United States Patent Application 20060116337).

The mice were treated intra-peritoneally with $CCl_4$ (0.5 ml/kg). They received GA (50, 300, 200, 400 mg/kg) 24 h and 0.5 h before and 4 h after administering $CCl_4$. This protection is likely due to the induction of heme oxygenase-1 and the down-regulation of pro-inflammatory mediators (Biol Pharm Bull. 2007, 30, 10, 11898). 18α-GA could dose-dependently inhibits $CCl_4$ induced liver fibrosis, by promoting the proliferation of hepatocytes, but inhibited that of Hepatic stellate cells (HSCs) GA blocks the translocation of NF-kB into the nucleus; this could suppress the activation and induce the apoptosis of HSCs (Q Ying, Med Sci. Monit., 2012, 18, 1: BR24).

GA was shown to attenuate histological hepatic changes and significantly reduced serum levels of AST, ALT, and lactic dehydrogenase (LDH), at all the indicated times. GA also significantly inhibited hepatocyte apoptosis by down-regulating the expression of caspase-3 and inhibiting the release of Cytochrome c from mitochondria into the cytoplasm. The anti-inflammatory activity of GA may rely on the inhibition of release of tumour necrosis factor-α, myeloperoxidase activity, and translocation of nuclear factor-kappa B into the nuclei. GA also up-regulated the expression of proliferating cell nuclear antigen, implying that it might be able to promote regeneration of livers harmed by LPS. In summary, GA may represent a potent drug protecting the liver against endotoxin-induced injury, especially after massive hepatectomy (Brazilian journal of Medical and Biological Research, 2007, 40, 1637). Pretreatment with GA (50 mg/kg) and the MMP inhibitor (5 mg/kg) suppressed increases in serum levels of ALT and AST in mice treated with LPS/Gal N due to a down-regulation of MMP-9 (J Pharm Pharmacol. 2008, 60, 1, 91).

The metabolic syndrome (MetS) is a cluster of metabolic abnormalities comprising visceral obesity, dyslipidaemia and insulin resistance (IR). Oral administration of 50 mg/kg of GA for one week could counteract the development of visceral obesity and improve dyslipidaemia via selective induction of tissue lipoprotein lipase (LPL), expression and a positive shift in serum lipid parameters respectively, and retard the development of IR associated with tissue steatosis (Lipids Health Dis. 2009, 29, 8, 31).

Diammoniumglycyrrhizinate (DG) protected mice against Concanavalin A (ConA)-induced elevation of serum ALT levels and apoptosis of hepatocytes; DG may possibly protect the liver from injury via two pathways: direct protection of hepatocytes from apoptosis through an IL-6 dependent way and indirect inhibition of T-cell-mediated inflammation through an IL-1 independent way (Int Immunopharmacol. 2007 October: 7(10): 1292).

Magnesium isoglycyrrhizinate 100 or 150 mg once daily, drugs are effective and safe treatment for chronic liver diseases (Zhoiighua Gan Zang Bing Za Zhi. 2009, 11, 847).

A sugar alcohol is a kind of alcohol prepared from sugars. These organic compounds are a class of polyols, also called polyhydric alcohol, polyalcohol, or glycitol. They are white, water-soluble solids that occur naturally and are used widely in the food industry as thickeners and sweeteners. Sugar alcohols such as Mannitol, Erythritol, Sorbitol, Xylitol etc., which are chemically stable can be used as a radical scavenger (hydroxyl radical). Similarly, it has been found that compounds like Erythritol, Mannitol, Sorbitol, Xylitol etc. up-regulated different types of superoxide dismutase (SOD) like Cu/Zn-, Mn- and EC-SOD isozymes. In particular, the SOD activity of the erythritol-added group increased by 2-5 times. Further it is reported that diabetics have a low SOD activity due to the Maillard reaction, because the Maillard reaction remarkably causes a decrease in the SOD activity (US Patent Application 20100037353 A1). Mannitol containing hyperosmolar solution has been shown to protect ethanol-induced gastric mucosal damage (Gharzouli K, Exp. Toxic. Pathol., 2001; 53: 175). Both rats and humans absorb and metabolize partially the Mannitol ingested in gastro intestinal tract (GIT). However, intestinal microflora convert Mannitol in to more absorbable form. In rat, absorbed mannitol is converted in to hepatic glycogen probably via fructose (J. Nutr. 1985, 115: 890). The mechanism of protecting living cells by Mannitol is not fully understood.

The beverage comprises of certain other ingredients like pH adjusting agent(s), and flavoring agent(s) etc.

Some important embodiments of the beverage of the present invention are as follows:

An important embodiment of the present invention relates to a beverage having reduced toxicity.

Yet another embodiment of the present invention relates to an alcoholic beverage having reduced hepato-toxicity.

Yet another embodiment of the present invention relates to an alcoholic beverage comprising hepato-protective agent(s) to achieve the reduced hepato-toxicity.

In an important embodiment of the present invention, the beverage comprises of 18β-Glycyrrhizin in combination with sugar alcohols selected from the group consisting D-Mannitol, D-Xylitol, D-Erythritol and mixtures thereof and reducing or non-reducing sugars selected from D-Xylose, D-Mannose, D-Sucrose and D-Lactose and mixtures thereof.

In yet another important embodiment of the present invention, the beverage comprises of 18α-Glycyrrhizin in combination with sugar alcohols selected from the group consisting D-Mannitol, D-Xylitol, D-Erythritol and mixtures thereof.

In an important embodiment, the beverage composition comprises 18β-Glycyrrhizin in the range of 0.05 to 0.4%, preferably 0.1 to 0.3% and D-Mannitol, D-Xylitol, D-Erythritol, D-Xylose, D-Mannose, D-Sucrose, D-Lactose and mixture thereof is in the range of 0.5 to 3.0%, preferably 1.0 to 2.5%.

In an important embodiment, the beverage composition comprises 18β-Glycyrrhizin in range of 0.05 to 0.3%, preferably 0.1 to 0.3% and D-Mannitol, D-Xylitol, D-Erythitol and mixtures thereof is in the range of 0.5 to 3.0%, preferably 1.0 to 2.5%.

In an important embodiment, the most preferable combination of hepato-protective agents is a combination of 18β-Glycyrrhizin or 18α-Glycyrrhizin and D-Mannitol.

In an important embodiment, the beverage composition comprises 18β-Glycyrrhizin in the range of 0.05 to 0.3% and the D-Mannitol is in the range of 0.5 to 3.0% and preferably 18β-Glycyrrhizin in the range of 0.1 to 0.3% and the D-Mannitol is in the range of 1.0 to 2.5%.

In an important embodiment, the beverage composition comprises 18α-Glycyrrhizin in the range of 0.1 to 0.3% and the D-Mannitol in the range of 1.0 to 2.5%.

In yet another embodiment, the process for the preparation of alcoholic beverage composition comprising steps of (a) obtaining alcohol or water or a mixture thereof, (b) mixing 18β-Glycyrrhizin or 18α-Glycyrrhizin with the alcohol or water or a mixture of alcohol and water of step (a), (c) adding sugar alcohol or sugar to the mixture of step (b), (d) adjusting the pH of the resulting solution of step (c) between 4.0-9.0, (e) optionally adding the flavoring agent and (t) obtaining the required alcoholic beverage composition.

Still another embodiment of the present invention is to provide an alcoholic beverage composition comprising the pH adjusting agent(s).

In yet another embodiment, the pH adjusting agent is an organic or inorganic base/buffer, preferably selected from potassium sorbate or sodium phosphate (monobasic or dibasic or tribasic).

Further embodiment of the present invention provides a beverage optionally comprising of flavoring agents selected from, vanilla and strawberry.

Still another embodiment of the present invention is to provide a beverage having acceptable taste, flavor, odor, clarity and buzz factor.

In a further embodiment of the present invention variation in dosages of sugar alcohols, glycyrrhizin and a combination of sugar alcohols and 18β or 18α-Glycyrrhizin has also been evaluated for its hepato-protective activity.

The scope of the present invention also includes the study in respect of acute and chronic hepatotoxicity caused by the variation in the alcohol dosage and its time of duration in administration.

Still another embodiment of the beverage composition relates to providing reduced hepato-toxicity.

Yet another embodiment of the beverage composition is the use in a method of amelioration of diseases involving acute and chronic toxicity such as alcoholic liver diseases (ALD) like steatosis, steatohepatitis, fibrosis, liver cirrhosis and hepatocellular carcinoma etc. which are caused by alcohol induced toxicity.

Another important embodiment of the present invention is that the beverage composition can be packed as ready-to-drink produce in food grade bottles, cans, tetra packs, pouches, etc. The packaging can be done by conventional methods.

For the establishment of synergism existing in the formulation of the present invention, markers/marker enzymes viz. SOD, Catalase, GPx, TNF-α were primarily taken into consideration for evaluating the % synergism. However, enzymes ALT, AST, ALKP and MDA were also analyzed to support the same.

Reasons for Estimating ALT, AST, ALKP:

Chronic misuse of alcohol changes marker enzymes of liver functions such as serum aspartate aminotransferase and alanine aminotransferase (AST, ALT), alkaline phosphatase (ALKP) and so these enzymes were studied.

ALT and AST are found in hepatocytes but AST is also found in skeletal and myocardial cells. In alcohol related liver damage, the AST is elevated more than the ALT, at least in part as a reflection of alcohol related skeletal damage. This is the reverse of the normal pattern in acute hepatocellular disease (for example acute viral hepatitis) where the ALT exceeds the AST.

ALKP is an enzyme in the cells lining the biliary ducts of the liver. ALKP levels in plasma will rise almost concomitantly with liver disease related with altered bile production and/or secretion and chronic liver diseases.

Reasons for Estimating Oxidative Stress Markers (MDA, Antioxidant Enzymes [SOD, CAT, Glutathione Peroxidase Etc.] Reduced Glutathione [GSH]):

Alcohol metabolism in the liver results in the formation reactive oxygen species (ROS). Alcohol also stimulates the activity of cytochrome P450, which contribute to ROS production. Further, alcohol can alter the levels of certain metals in the body, thereby facilitating ROS production. Finally, alcohol reduces the levels of agents that can eliminate ROS (i.e., endogenous antioxidants). The resulting state of the cell, known as oxidative stress, can lead to cell injury. ROS production and oxidative stress in liver cells play a central role in the development of alcoholic liver disease.

MDA (Malondialdehyde) is the end product of cell membrane lipid peroxidation. ROS degrade (oxidative degradation) polyunsaturated fatty acids of cell membrane resulting cell damage. The extent of lipid peroxidation can be well correlated with tissue MDA content.

SOD (Superoxide dismutase) catalyzes the breakdown of the superoxide radical into oxygen and hydrogen peroxide. Liver cells are enriched with SOD as it is the major organ related with metabolism numerous substances.

CAT (Catalase) catalyzes the conversion of hydrogen peroxide ($H_2O_2$) to water and oxygen. This enzyme is localized to peroxisomes in most eukaryotic cells.

GPx (Glutathione peroxidase) is the most abundantly available in the cytoplasm of most of the cells. It neutralizes hydrogen peroxide ($H_2O_2$) in presence of GSH.

$$2GSH \quad + \quad H_2O_2 \quad \xrightarrow{GPx} \quad GS\text{-}SG \quad + \quad 2H_2O_2$$

(GSH-reduced glutathione, GSSG-oxidized glutathione)

GSH is the most abundant antioxidant in aerobic cells. GSH is critical for protecting the cells from oxidative stress, acting as a free radical scavenger and inhibitor of lipid peroxidation. (GSH also participates in the degradation of $H_2O_2$ by glutathione peroxidases (GPx). The ratio of reduced glutathione (GSH) to oxidized glutathione (GSSG) is an indicator of cellular health (status of cellular redox potential). In normal healthy conditions GSH constituting nearly 90% of cellular glutathione (i.e., GSH/GSSG is around 9). However, the GSH/GSSG ratio is reduced in ROS related disorders.

Reasons for Estimating Tumor Necrotic Factor Alpha (TNF-α):

Alcohol consumption increases the translocation of endotoxins from intestine to portal circulation and interacts with Kuppfer cells (immunocytes) leading to secretion of several pro-inflammatory cytokines including tumor necrotic factor alpha (TNF-α).

Based on the Above Description, we Identified Some Key Marker and Justify the Importance of the Parameter Chosen:

SOD, Catalase & GPx: In system SOD catalyzes the dismutation of superoxide to $H_2O_2$. GPx and Catalase then independently convert this $H_2O_2$ to water. SOD together with GPx and catalase form the main enzyme defense against harmful effect of ROS.

GSH is the main endogenous antioxidant that protects cells from xenobiotics including alcohol. Alcohol is known to deplete GSH levels on the process to neutralize oxidants. Apart from this, endogenous glutathione-glutathione peroxidase system acts as an important antioxidants and cyto-protective machinery in the hepatocytes exposed to ethanol. Thus, depletion of cellular GSH level plays an important role in ethanol-mediated hepato-cellular dysfunction.

The following tables (1 to 9) illustrate the % of hepatoprotection of individual ingredients, combination of ingredients and the % synergism exhibited using respective combinations. All animal experiments were conducted for a period of one month by per oral administration of 2.5 g/kg dose of alcohol.

TABLE 1

% Protection of D-Mannitol

| Sample Code | Man % | GSH % Prot. | SOD etc. % Prot. | TNF-α % Prot. | ALT etc % Prot. | MDA % Prot. |
|---|---|---|---|---|---|---|
| A | 0.5 | 10.35 | 12.71 | 7.19 | 12.26 | 19.17 |
| 3 | 1 | 20.06 | 19.32 | 16.74 | 20.37 | 31.63 |
| B | 1.5 | 25.76 | 26.21 | 29.89 | 25.94 | 48.56 |
| C | 2.5 | 31.53 | 35.83 | 31.46 | 29.71 | 50.8 |
| 11 | 3 | 32.37 | 36.08 | 30.76 | 29.48 | 50.31 |

TABLE 2

% Protection of D-Xylitot & D-Erythritol

| | GSH % Prot. | SOD etc % Prot. | TNF-α % Prot. | ALT etc % Prot. | MDA % Prot. |
|---|---|---|---|---|---|
| Xyl % | | | | | |
| 1% | 19.76 | 18.91 | 15.77 | 17.62 | 26.9 |
| 2.5% | 35.57 | 36.88 | 30.05 | 26.72 | 45.38 |
| Ery % | | | | | |
| 1% | 18.71 | 17.94 | 16.57 | 17.84 | 24.71 |
| 2.5% | 37.29 | 36.29 | 35.96 | 32.13 | 48.61 |

TABLE 3

% Comparative Protection of 18β and 1.8α-Glycyrrhizin

| Sample Code | GA % | GSH % Prot. | SOD etc % Prot. | TNF-α % Prot. | ALT etc % Prot. | MDA Prot. % |
|---|---|---|---|---|---|---|
| 18β-GA | | | | | | |
| D | 0.1 | 3.29 | 11.45 | 7.64 | 8.38 | 15.97 |
| U | 0.2 | 12.1 | 16.72 | 12.31 | 13.25 | 27.12 |
| W | 0.3 | 19.1 | 27.95 | 21.18 | 20.99 | 46.35 |
| X | 0.4 | 31.34 | 31.05 | 29.28 | 26.42 | 56.74 |
| 18α-GA | | | | | | |
| 4 | 0.1 | 8.93 | 14.33 | 10.58 | 11.98 | 15.1 |
| 5 | 0.3 | 16.96 | 25.84 | 23.45 | 18.3 | 41.69 |

TABLE 4

% Protection and % Synergism of 18β-Glycyrrhizin-Mannitol combinations

| Sample Code | GA % | Man % | GSH % Prot. | GSH % Syn. | SOD etc % Prot. | SOD etc % Syn | TNF-α % Prot. | TNF-α % Syn | ALT etc. % Prot. | ALT etc. % Syn | MDA % Prot. | MDA % Syn |
|---|---|---|---|---|---|---|---|---|---|---|---|---|
| H | 0.1 | 2.5 | 48.24 | 38.51 | 60.15 | 26.65 | 50.56 | 29.31 | 40.35 | 10.52 | 85.62 | 28.23 |
| L | 1 | 2.5 | 83.29 | 10.45 | 78.75 | 21.31 | 87.64 | 29.99 | 52.35 | −11.15 | 93.29 | −20.87 |
| O | 0.3 | 2.5 | 61.95 | 22.43 | 71.57 | 13.44 | 69.63 | 32.28 | 49.4 | −1.09 | 76.54 | −21.21 |
| M | 0.4 | 2.5 | 76.38 | 21.55 | 79.83 | 20.59 | 81.62 | 34.38 | 53.15 | −4.17 | 80.41 | −25.21 |
| C | 0.1 | 0.5 | 17.64 | 28.76 | 25.34 | 3.72 | 19.16 | 29.2 | 21 | 7.32 | 39.63 | 12.78 |
| 4 | 0.1 | 1 | 29.58 | 26.68 | 39.33 | 28.1 | 32.68 | 34.04 | 29.13 | 5.25 | 55.41 | 16.41 |
| 12 | 0.1 | 3 | 45.53 | 27.68 | 58.15 | 22.74 | 47.2 | 22.92 | 37.23 | 0.37 | 70.87 | 6.93 |

TABLE 5

Comparative % Protection and % Synergism of 18β or 18α-Glycyrrhizin - Mannitol combinations

| Sample Code | | Man % | GSH % Prot. | GSH Syn % | SOD etc % Prot. | SOD etc % Syn | TNF-α % Prot. | TNF-α % Syn | ALT etc % Prot. | ALT etc % Syn | MDA % Prot. | MDA Syn % |
|---|---|---|---|---|---|---|---|---|---|---|---|---|
| 18β-GA % | | | | | | | | | | | | |
| 4 | 0.1 | 1 | 29.58 | 26.68 | 39.33 | 28.1 | 32.68 | 34.04 | 29.13 | 5.25 | 55.41 | 16.41 |
| H | 0.1 | 2.5 | 48.24 | 38.51 | 60.15 | 26.65 | 50.56 | 29.31 | 40.35 | 10.52 | 85.62 | 28.23 |
| O | 0.3 | 2.5 | 61.95 | 22.43 | 71.57 | 13.44 | 69.63 | 32.28 | 49.4 | −1.09 | 76.54 | −21.21 |

TABLE 5-continued

Comparative % Protection and % Synergism of 18β or 18α-Glycyrrhizin - Mannitol combinations

| Sample Code | | Man % | GSH % Prot. | GSH Syn % | SOD etc % Prot. | SOD etc % Syn | TNF-α % Prot. | TNF-α % Syn | ALT etc % Prot. | ALT etc % Syn | MDA % Prot. | MDA Syn % |
|---|---|---|---|---|---|---|---|---|---|---|---|---|
| | 1.8α-GA % | | | | | | | | | | | |
| 6 | 0.1 | 1 | 32.74 | 12.94 | 42.42 | 26.01 | 34.05 | 24.63 | 30.97 | −0.29 | 54.16 | 15.9 |
| 8 | 0.1 | 2.5 | 52.68 | 30.2 | 60.16 | 19.8 | 53.21 | 26.57 | 41.35 | 3.51 | 76.6 | 16.24 |
| 10 | 0.3 | 2.5 | 57.44 | 18.46 | 69.06 | 12.57 | 68.1 | 24.02 | 46.49 | −1.35 | 75.8 | −18.05 |

TABLE 6

Comparative % Protection and % Synergism of 18β-Glycyrrhizin-Mannitol, Xylitol & Erythritol)

| | | SOD etc. % Prot. | SOD etc. % Syn | GSH % Prot. | GSH % Syn | TNF-α % Prot. | TNF-α % Syn |
|---|---|---|---|---|---|---|---|
| 0.10% | 1% | | | | | | |
| GA % | Man % | 39.33 | 28.1 | 29.58 | 26.68 | 32.68 | 34.04 |
| GA % | Ery % | 35.64 | 21.5 | 28.85 | 31.14 | 30.37 | 25.44 |
| GA % | Xyl % | 38.26 | 26.35 | 28.19 | 22.3 | 29.72 | 26.95 |
| Man: Ery | | — | 1.3 | — | 0.85 | — | 1.33 |
| Man: Xyl | | — | 1.06 | — | 1.19 | — | 1.26 |
| 0.10% | 2.50% | | | | | | |
| GA % | Man % | 60.15 | 26.65 | 48.24 | 38.51 | 50.56 | 29.31 |
| GA % | Ery % | 56.47 | 18.21 | 43.35 | 6.83 | 49.26 | 12.98 |
| GA % | Xyl % | 56.94 | 17.61 | 44.8 | 15.29 | 46.29 | 22.82 |
| Man: Ery | | — | 1.46 | — | 5.63 | — | 2.25 |
| Man: Xyl | | — | 1.51 | — | 2.51 | — | 1.28 |
| 0.30% | 2.50% | | | | | | |
| GA % | Man % | 71.57 | 13.44 | 61.95 | 22.43 | 69.63 | 32.28 |
| GA % | Ery % | 71.86 | 11.94 | 66.14 | 17.29 | 64.36 | 12.64 |
| GA % | Xyl % | 71.18 | 10.04 | 60.61 | 10.87 | 55.65 | 8.63 |
| Man: Ery | | — | 1.12 | — | 1.29 | — | 2.55 |
| Man: Xyl | | — | 1.33 | — | 2.06 | — | 3.74 |

TABLE 7

Comparative data of % Protection and % Synergism of (18β Glycyrrhizin/Mannitol, Xylitol and Erythritol)

| | | ALT etc % Prot. | ALT etc % Syn | MDA % Prot. | MDA % Syn |
|---|---|---|---|---|---|
| 0.10% | 1% | | | | |
| GA % | Man % | 29.13 | 5.25 | 55.41 | 16.41 |
| GA % | Ery % | 24.48 | −5.83 | 46.38 | 14.01 |
| GA % | Xyl % | 27.19 | 6.63 | 50.02 | 16.68 |
| 0.10% | 2.50% | | | | |
| GA % | Man % | 40.35 | 10.52 | 85.62 | 28.23 |
| GA % | Ery % | 40.06 | −0.62 | 75.29 | 16.58 |
| GA % | Xyl % | 38.2 | 10.18 | 76.51 | 24.71 |
| 0.30% | 2.50% | | | | |
| GA % | Man % | 49.4 | −1.09 | 76.54 | −21.21 |
| GA % | Ery % | 52.68 | −0.89 | 80.3 | −15.44 |
| GA % | Xyl % | 46.9 | −1.86 | 80.52 | −12.22 |

TABLE 8

% Protection of Sucrose, Mannose, Xylose & Lactose

| | GSH % Prot. | SOD etc % Prot. | TNF-α % Prot. | ALT etc % Prot. | MDA % Prot. |
|---|---|---|---|---|---|
| Suc % | | | | | |
| 1 | 6 | 5.16 | 6.13 | 6.70 | 8.27 |
| 2.5 | 11.63 | 10.49 | 14.18 | 13.89 | 18.92 |
| Mans % | | | | | |
| 1 | 6.12 | 3.93 | 7.85 | 6.14 | 10.65 |
| 2.5% | 13.59 | 11.18 | 16.49 | 16.34 | 23.67 |
| Xyls % | | | | | |
| 1 | 6.23 | 7.83 | 6.44 | 8.06 | 6.28 |
| 2.5 | 11.84 | 19.1 | 13.98 | 14.73 | 15.38 |
| Lac % | | | | | |
| 1 | 4.36 | 6.78 | 8.19 | 8.21 | 7.70 |
| 2.5 | 14.8 | 17.38 | 15.26 | 17.41 | 21.47 |

TABLE 9

% Protection and % Synergism of (18β-GA: Sucrose, Mannose, Xylose & Lactose)

| Sample Code | GA % | | GSH % Prot. | GSH % Syn | SOD etc % Prot. | SOD etc % Syn | TNF-α % Prot. | TNF-α % Syn | ALT etc % Prot. | ALT etc % Syn | MDA % Prot. | MDA % Syn |
|---|---|---|---|---|---|---|---|---|---|---|---|---|
| | | Suc % | | | | | | | | | | |
| 10 | 0.1 | 1 | 10.65 | 14.64 | 18.32 | 10.37 | 15.14 | 9.95 | 14.63 | 1.69 | 25.87 | 6.72 |
| 11 | 0.3 | 2.5 | 33.41 | 8.72 | 41.3 | 8.37 | 40.12 | 13.46 | 31.4 | −7.47 | 56.53 | −13.39 |
| | | Mans % | | | | | | | | | | |
| 14 | 0.1 | 1 | 11.02 | 17.11 | 18.05 | 17.29 | 17.07 | 10.2 | 15.71 | 8.66 | 28.82 | 8.26 |
| 15 | 0.3 | 2.5 | 37.58 | 14.96 | 42.02 | 9.16 | 43.19 | 14.65 | 33.88 | −7.97 | 59.27 | −15.35 |

TABLE 9-continued

% Protection and % Synergism of (18β-GA: Sucrose, Mannose, Xylose & Lactose)

| Sample Code | GA % | | GSH % Prot. | GSH % Syn | SOD etc % Prot. | SOD etc % Syn | TNF-α % Prot. | TNF-α % Syn | ALT etc % Prot. | ALT etc % Syn | MDA % Prot. | MDA % Syn |
|---|---|---|---|---|---|---|---|---|---|---|---|---|
| | | Xyls % | | | | | | | | | | |
| 18 | 0.1 | 1 | 10.9 | 14.05 | 20.97 | 8.83 | 15.6 | 10.8 | 16.84 | 4.26 | 22.23 | −0.09 |
| 19 | 0.3 | 2.5 | 34.27 | 10.76 | 53.23 | 13.21 | 38.1 | 8.36 | 32.28 | −9.47 | 52.64 | −14.66 |
| | | Lac % | | | | | | | | | | |
| 22 | 0.1 | 1 | 8.57 | 12.03 | 19.47 | 6.79 | 17.2 | 8.65 | 16.75 | 3.17 | 25.1 | 6.04 |
| 23 | 0.3 | 2.5 | 38.16 | 12.57 | 47.19 | 5.07 | 39.55 | 8.53 | 34.6 | −9.98 | 57.88 | −14.66 |

The data provided in the above tables clearly indicates that the 18β-GA/D-Mannitol combination exhibits superior order of synergism over the combination of 18β-GA/D-Erythritol and 18β-GA/Xylitol combinations.

The data provided in the above tables also indicates that overall the 18β-GA/D-Mannitol combinations exhibit almost similar order of synergism as that of 18α-GA/D-Mannitol combinations.

Also it can be concluded that the combination of 18β-GA/reducing or non-reducing mono or disaccharide has exhibited lesser degree of synergistic effect.

The present invention is illustrated with the following examples. However, it should be understood that the scope of the present invention is not limited by the examples in any manner. It will be appreciated by any person skilled in this art that the present investigation includes following examples and further can be modified and altered within the scope of the present invention.

Materials and Methods
Reagents

Distilled ethanol was obtained from Bengal Chemicals, West Bengal, India. Biochemical kits like AST, ALT, ALKP and total protein were obtained from Span Diagnostics Ltd. Surat, India. Time course study of oxidative and nitrosative stress and antioxidant enzymes in $K_2Cr_2O_7$-induced nephrotoxicity. BMC Nephrol., 6: 4). TNF-α was estimated by standard procedures as mentioned in Rat TNF-α ELISA kit (Bio Legend, Inc. San Diego, Calif., USA).

All the chemicals used in the present study were of analytical grade and obtained from the following companies: Sigma (St. Louis, Mo. USA), Merck (Mumbai, India), S. D. Fine Chemicals (Mumbai, India) and Qualign (Mumbai, India).

Alcohol Induced Sub-Acute Hepatotoxicity in Rats

Male Wistar albino rats weighing 150-200 g are procured from local registered traders (CPCSEA Regd No. 1443/po/6/4/CPCSEA), Kolkata. India and were acclimatized for 7 days at standard housing condition (26° C.±2° C., 60-70% RH with 12±1 hours light and dark cycle). Animals were fed with commercially available diet (Upton India Pvt. Ltd, India) and water ad-libitum during the experiment period.

EXAMPLES

Example 1 a) Model for Biological Testing

Male Wistar albino rats weighing 150-200 g are procured and randomly divided into groups consisting of six animals in each group. Sub-acute toxicity is induced by alcohol in rats by oral administration of 25% alcohol (2.5 gm/kg/day, p.o.) for 28 days and this group served as the negative control and the positive control group received distilled water only.

b) Preparation of Drug Solution

All drug solutions were prepared in 15-40% aqueous alcohol, adjusting the pH in the range of 4.0-9.0 for evaluation of hepato-protective activity. This solution is further diluted with distilled water to obtain 25%, aqueous alcoholic solution and administered orally by gavage to different rats group of step (a).

c) Evaluation of Hepato-Protective Activity

On day $28^{th}$ day the animals are anaesthetized with ether and blood samples are collected by cardiac puncture and the serum is used for the assay of marker enzymes viz. serum alanine aminotransferase (ALT), aspartate aminotransferase (AST), alkaline phosphatase (ALP). The rats are sacrificed by exposure to an overdose of ether, immediately after the collection of blood; their livers are removed, washed in cold saline. Part of the liver is used for preparation of liver homogenate in phosphate buffer (pH 7.4). The supernatant is used for the estimation of malondialdehyde (MDA), super oxide dismutase (SOD), catalase (CAT), reduced glutathione (GSH), and Glutathione peroxidase (GPx).

Example 2

D-Mannitol (0.5 g) is dissolved in aqueous alcohol (100 ml) to provide 0.5% solution. This solution is administered in several portions to one of the rats group of Example (1a). The administration is carried out over a period of 28 days; each day 10 ml sample is diluted with 6 nil distilled water to make 25% aqueous alcoholic solution (16 ml) and fed orally (10 ml/kg/day). Evaluation of hepato-protective activity is carried out as per Example (1c).

| Mean % hepato-protection: | |
|---|---|
| ALT, AST and ALKP | 12.26% |
| SOD, CAT and GPx | 12.71% |
| GSH | 10.35% |
| Hepatic MDA | 19.17% |
| TNF-α | 7.19% |

Example 3

D-Mannitol (2.5 g) is dissolved in aqueous alcohol (100 ml) to provide 2.5% solution. This solution is administered in several portions to one of the rats group of Example (1a). The administration, sample dilution, oral feeding and evaluation of hepato-protective activity is carried out as mentioned in Example 2 and as per Example (1c).

| Mean % hepato-protection: | |
|---|---|
| ALT, AST and ALKP | 29.71% |
| SOD, CAT and GPx | 35.83% |
| GSH | 31.53% |
| Hepatic MDA | 50.80% |
| TNF-α | 31.46% |

Example 4

18β-Glycyrrhizin (0.1 g) is dissolved in aqueous alcohol (100 ml) to provide 0.1% solution. This solution is administered in several portions to one of the of rats group of Example (1a). The administration, sample dilution, oral feeding and evaluation of hepato-protective activity is carried out as mentioned in Example 2 and as per Example (1c).

| Mean % hepato-protection | |
|---|---|
| ALT, AST and ALKP | 8.38% |
| SOD, CAT and GPx | 11.45% |
| GSH | 3.29% |
| Hepatic MDA | 15.97% |
| TNF-α | 7.64% |

Example 5

D-Mannitol (2.5 g) and 18β-Glycyrrhizin (0.1 g) are dissolved in aqueous alcohol (100 ml) to provide 2.6% solution. This solution is administered in several portions to one of the rats group of Example (1a). The administration, sample dilution, oral feeding and evaluation of hepato-protective activity is carried out as mentioned in Example 2 and as per Example (1c).

| Mean % hepato-protection: | |
|---|---|
| ALT, AST and ALKP | 40.35% |
| SOD, CAT and GPx | 60.15% |
| GSH | 48.24% |
| Hepatic MDA | 85.62% |
| TNF-α | 50.56% |

Example 6

D-Mannitol (2.5 g) and 18β-Glycyrrhizin (1.0 g) are dissolved in aqueous alcohol (100 ml) to provide 3.5% solution. This solution is administered in several portions to one of the rats groups of Example 1(a). The administration, sample dilution, oral feeding and evaluation of hepato-protective activity is carried out as mentioned in Example 2 and as per Example (1c).

| Mean % hepato-protection: | |
|---|---|
| ALT, AST and ALKP | 52.35% |
| SOD, CAT and GPx | 78.75% |
| GSH | 83.29% |
| Hepatic MDA | 93.29% |
| TNF-α | 87.64% |

Example 7

D-Mannitol (0.5 g) and 18β-Glycyrrhizin (0.1 g) are dissolved in aqueous alcohol (100 ml) to provide 0.6% solution. This solution is administered in several portions to one of the rats group of Example (1a). The administration, sample dilution, oral feeding and evaluation of hepato-protective activity is carried out as mentioned in Example 2 and as per Example (1c).

| Mean % hepato-protection: | |
|---|---|
| ALT, AST and ALKP | 21.0% |
| SOD, CAT and GPx | 25.34% |
| GSH | 17.64% |
| Hepatic MDA | 39.63% |
| TNF-α | 19.16% |

Example 8

D-Mannitol (3.0 g) and 18β-Glycyrrhizin (0.1 g) are dissolved in aqueous alcohol (100 ml) to provide 3.1% solution. This solution is administered in several portions to one of the rats group of Example (1a). The administration, sample dilution, oral feeding and evaluation of hepato-protective activity is carried out as mentioned in Example 2 and as per Example (1c).

| Mean % hepato-protection: | |
|---|---|
| ALT, AST and ALKP | 37.23% |
| SOD, CAT and GPx | 58.15% |
| GSH | 45.53% |
| Hepatic MDA | 70.87% |
| TNF-α | 47.20% |

Example 9

D-Mannitol (2.5 g) and 18β-Glycyrrhizin (0.4 g are dissolved in aqueous alcohol (100 ml) to provide 2.9% solution. This solution is administered in several portions to one of the rats group of Example (1a). The administration, sample dilution, oral feeding and evaluation of hepato-protective activity is carried out as mentioned in Example 2 and as per Example (1c).

| Mean % hepato-protection: | |
|---|---|
| ALT, AST and ALKP | 53.15% |
| SOD, CAT and GPx | 79.83% |
| GSH | 76.38% |
| Hepatic MDA | 80.41% |
| TNF-α | 81.62% |

Example 10

D-Mannitol/D-Xylitol/D-Erythritol (1.0 g) and 18β-Glycyrrhizin (0.1 g) are dissolved in aqueous alcohol (100 ml) to provide 1.1% solution. This solution is administered in several portions to one of the rats group of Example (1a). The administration, sample dilution, oral feeding and evaluation of hepato-protective activity is carried out as mentioned in Example 2 and as per Example (1c).

| Mean % hepato-protection: | | | |
|---|---|---|---|
| | Sugar alcohols | | |
| Enzymes/Markers | D-Mannitol | D-Xylitol | D-Erythritol |
| ALT, AST and ALKP | 29.13% | 27.19% | 24.48% |
| SOD, CAT and GPx | 39.33% | 38.26% | 35.64% |
| GSH | 29.58% | 28.19% | 28.25% |
| Hepatic MDA | 55.41% | 50.02% | 46.38% |
| TNF-α | 32.68% | 29.72% | 30.37% |

Example 11

D-Mannitol/D-Xylitol/D-Erythritol (2.5 g) and 18β-Glycyrrhizin (0.3 g) are dissolved in aqueous alcohol (100 ml) to provide 2.8% solution. This solution is administered in several portions to one of the rats group of Example (1a). The administration, sample dilution, oral feeding and evaluation of hepato protective activity is carried out as mentioned in Example 2 and as per Example (1c).

| Mean % hepato-protection: | | | |
|---|---|---|---|
| | Sugar alcohols | | |
| Enzymes/Markers | D-Mannitol | D-Xylitol | D-Erythritol |
| ALT, AST and ALKP | 49.40% | 46.90% | 52.68% |
| SOD, CAT and GPx | 71.57% | 71.18% | 71.86% |
| GSH | 61.95% | 60.61% | 66.14% |
| Hepatic MDA | 76.54% | 80.52% | 80.30% |
| TNF-α | 69.63% | 55.65% | 64.36% |

Example 12

DI-Mannose/D-Xylose/D-Lactose/D-Sucrose (2.5 g) and 18β-Glycyrrhizin (0.3 g) are dissolved in aqueous alcohol (100 ml) to provide 2.8% solution. This solution is administered in several portions to one of the rats group of Example (1a). The administration, sample dilution, oral feeding and evaluation of hepato-protective activity is carried out as mentioned in Example 2 and as per Example (1c).

| Mean % hepato-protection: | | | | |
|---|---|---|---|---|
| | Sugars | | | |
| Enzymes/Markers | D-Mannose | D-Xylose | D-Lactose | D-Sucrose |
| ALT, AST and ALKP | 33.88% | 32.28% | 34.60% | 31.40% |
| SOD, CAT and GPx | 42.02% | 53.23% | 47.19% | 41.30% |
| GSH | 37.58% | 34.27% | 38.16% | 33.41% |
| Hepatic MDA | 59.27% | 52.64% | 57.88% | 56.53% |
| TNF-α | 43.19% | 38.10% | 39.55% | 40.12% |

Example 13

D-Mannose/D-Xylose/D-lactose/D-Sucrose (1.0 g) and 18β-Glycyrrhizin (0.1 g) are dissolved in aqueous alcohol (100 ml) to provide 1.1% solution. This solution is administered in several portions to one of the rats group of Example (1a). The administration, sample dilution, oral feeding and evaluation of hepato-protective activity is carried out as mentioned in Example 2 and as per Example (1c).

| Mean % hepato-protection: | | | | |
|---|---|---|---|---|
| | Sugars | | | |
| Enzymes/Markers | D-Mannose | D-Xylose | D-Lactose | D-Sucrose |
| ALT, AST and ALKP | 15.71 | 16.84% | 16.75% | 14.63% |
| SOD, CAT and GPx | 18.05 | 20.97% | 19.47% | 18.32% |
| GSH | 11.02 | 10.90% | 8.57% | 10.65% |
| Hepatic MDA | 28.82 | 22.23% | 25.10% | 25.87% |
| TNF-α | 17.07 | 15.60% | 17.20% | 15.14% |

Example 14

D-Mannitol (1.0 g) and 18α-Glycyrrhizin (0.1 g) are dissolved in aqueous alcohol (100 ml) to provide 1.1% solution. This solution is administered in several portions to one of the rats group of Example (1a). The administration, sample dilution, oral feeding and evaluation of hepato-protective activity is carried out as mentioned in Example 2 and as per Example (1c).

| Mean % hepato-protection: | |
|---|---|
| ALT, AST and ALKP | 30.97% |
| SOD, CAT and GPx | 42.42% |
| GSH | 32.74% |
| Hepatic MDA | 54.16% |
| TNF-α | 34.05% |

Example 15

D-Mannitol (2.5 g) and 18α-Glycyrrhizin (0.3 g) are dissolved in aqueous alcohol (100 ml) to provide 2.8% solution. This solution is administered in several portions to one of the rats group of Example (1a). The administration, sample dilution, oral feeding and evaluation of hepato-protective activity is carried out as mentioned in Example 2 and as per Example (1c).

| Mean % hepato-protection: | |
|---|---|
| ALT, AST and ALKP | 46.49% |
| SOD, CAT and GPx | 69.06% |
| GSH | 57.44% |
| Hepatic MDA | 78.80% |
| TNF-α | 68.1% |

Example 16

Method of Preparation:

0.1 to 0.4 grams of 18β/α-Glycyrrhizin is dissolved in 15-40% alcohol or alcohol:water mixture (in 100 ml). To this solution (0.5 to 3.0 grams) of sugar alcohol or sugar is added. The resulting solution is mixed thoroughly to obtain a clear solution. Thereafter the pH of the resulting solution is adjusted to between 4.0-9.0 and optionally desired flavoring agent (vanilla) is added to obtain the final alcoholic beverage composition.

The expansion for the abbreviations used in this application is enumerated as below:
GA: Glycyrrhizin (Glycyrrhizic acid or Glycyrrhizinic acid or 18β-Glycyrrhizin)
Man: Mannitol
Xyl: Xylitol Ery: Erythritol
Mans: Mannose
Suc: Sucrose
Xyls: Xylose
Lac: Lactose
SOD etc: SOD, CAT & GPx
ALT etc: ALT, AST and ALKP
Mat: Matrine

ADVANTAGES OF THE PRESENT INVENTION

1. The alcoholic beverage of the present invention has better hepato-protection.
2. The alcoholic beverage of the present invention has an acceptable odor, taste, clarity and acceptable buzz factor.

What is claimed is:

1. An alcoholic beverage composition providing synergistic hepato-protection, the alcoholic beverage comprising:
    a) a first hepato-protective agent;
    b) alcohol or an alcohol-water combination; and
    c) a second hepato-protective agent;
    d) wherein said first hepato-protective agent comprises 18α-Glycyrrhizin in a mass concentration range of 0.05% to 0.3% or 18β-Glycyrrhizin in a mass concentration range of 0.05% to 0.4% or a combination thereof;
    e) wherein said second hepato-protective agent comprises at least one sugar or at least one sugar alcohol in a mass concentration range of 0.5% to 3.0%.

2. The alcoholic beverage composition as claimed in claim 1, wherein said second hepato-protective agent comprises at least one sugar alcohol selected from the group consisting of D-Mannitol, D-Xylitol, and D-Erythritol, or a combination thereof.

3. The alcoholic beverage composition as claimed in claim 1, wherein said second hepato-protective agent comprises at least one sugar selected from the group consisting of D-Sucrose, D-Mannose, D-Xylose and D-Lactose, or a combination thereof.

4. The alcoholic beverage composition as claimed in claim 2, wherein: said first hepato-protective agent comprises 18α-Glycyrrhizin in a mass concentration range of 0.05% to 0.3%; and said sugar alcohol is in a mass concentration range of 0.5% to 3.0%.

5. The alcoholic beverage composition as claimed in claim 2, wherein: said first hepato-protective agent comprises 18α-Glycyrrhizin in a mass concentration range of 0.1% to 0.3%; and said sugar alcohol is in a mass concentration range of 1.0% to 2.5%.

6. The alcoholic beverage composition as claimed in claim 3 wherein: said first hepato-protective agent comprises 18α-Glycyrrhizin in a mass concentration range of 0.05 to 0.3%; and said sugar is in a mass concentration range of 0.5% to 3.0%.

7. The alcoholic beverage composition as claimed in claim 3, wherein: said first hepato-protective agent comprises 18α-Glycyrrhizin in a mass concentration range of 0.1% to 0.3%; and said sugar is in a mass concentration range of 1.0% to 2.5%.

8. The alcoholic beverage composition as claimed in claim 1, further comprising at least one pH adjusting agent.

9. The alcoholic beverage composition as claimed in claim 1, herein said alcoholic beverage composition further comprises at least one flavoring agent.

10. A process for the preparation of alcoholic beverage composition of claim 1, comprising steps of (a) obtaining alcohol or alcohol-water combination, (b) mixing 18β-Glycyrrhizin or 18α-Glycyrrhizin with the alcohol or alcohol-water combination of step (a), (c) adding sugar alcohol or sugar to the mixture of step (b), (d) adjusting pH of resulting solution of step (c) between 4.0-9.0, (e) optionally adding flavoring agent and (f) obtaining the alcoholic beverage composition.

11. A method of using the alcoholic beverage composition as claimed in claim 1, comprising the step of consuming the alcoholic beverage composition by a human, for providing reduced hepato-toxicity in said human.

12. The alcoholic beverage composition as claimed in claim 1 for use in a method of amelioration of diseases involving acute and chronic toxicity caused by alcohol consumption.

13. The alcoholic beverage composition claimed in claim 9, wherein said flavoring agent comprises vanilla flavor or strawberry flavor.

14. The alcoholic beverage composition as claimed in claim 2, wherein: said first hepato-protective agent comprises 18β-Glycyrrhizin in a mass concentration range of 0.05% to 0.4%; and said sugar alcohol is in a mass concentration range of 0.5% to 3.0%.

15. The alcoholic beverage composition as claimed in claim 2, wherein: said first hepato-protective agent comprises 18β-Glycyrrhizin in a mass concentration range of 0.1% to 0.3%; and said sugar alcohol is in a mass concentration range of 1.0% to 2.5%.

16. The alcoholic beverage composition as claimed in claim 3, wherein: said first hepato-protective agent comprises 18β-Glycyrrhizin in a mass concentration range of 0.05 to 0.4%; and said sugar is in a mass concentration range of 0.5% to 3.0%.

17. The alcoholic beverage composition as claimed in claim 3, wherein: said first hepato-protective agent comprises 18β-Glycyrrhizin in a mass concentration range of 0.1% to 0.3%; and said sugar is in a mass concentration range of 1.0% to 2.5%.

18. The alcoholic beverage composition as claimed in claim 1, wherein said first hepato-protective agent comprises 18β-Glycyrrhizin or 18α-Glycyrrhizin and said second hepato-protective agent comprises D-Mannitol.

19. The alcoholic beverage composition as claimed in claim 18, wherein: said first hepato-protective agent comprises 18β-Glycyrrhizin in a mass concentration range of 0.05% to 0.4%; and said D-Mannitol is in a mass concentration range of 0.5% to 3.0%.

20. The alcoholic beverage composition as claimed in claim 18, wherein: said first hepato-protective agent comprises 18β-Glycyrrhizin in a mass concentration range of 0.1% to 0.3%; and said D-Mannitol is in a mass concentration range of 1.0% to 2.5%.

21. The alcoholic beverage composition as claimed in claim 18, wherein: said first hepato-protective agent comprises 18α-Glycyrrhizin in a mass concentration range of 0.05% to 0.3%; and said D-Mannitol is in a mass concentration range of 0.5% to 3.0%.

22. The alcoholic beverage composition as claimed in claim 18, wherein: said first hepato-protective agent comprises 18α-Glycyrrhizin in a mass concentration range of 0.1% to 0.3%; and said D-Mannitol is in a mass concentration range of 1.0% to 2.5%.

23. The alcoholic beverage composition as claimed in claim 8, wherein said pH adjusting agent comprises an organic or inorganic base/buffer selected from the group consisting of potassium sorbate, sodium dihydrogen phosphate, sodium hydrogen phosphate, and trisodium phosphate.

* * * * *